(12) United States Patent
Phillips

(10) Patent No.: US 6,887,197 B2
(45) Date of Patent: May 3, 2005

(54) SIDE LOADING SURGICAL RETRACTOR HAVING OFFSET CAVITY

(75) Inventor: Burns Phillips, Nashville, TN (US)

(73) Assignee: BOSS Instruments Ltd., Nashville, TN (US)

( * ) Notice: Subject to any disclaimer, the term of this patent is extended or adjusted under 35 U.S.C. 154(b) by 0 days.

(21) Appl. No.: 10/357,676

(22) Filed: Feb. 4, 2003

(65) Prior Publication Data

US 2003/0120132 A1 Jun. 26, 2003

Related U.S. Application Data

(63) Continuation-in-part of application No. 10/117,929, filed on Apr. 5, 2002, now Pat. No. 6,733,444.
(60) Provisional application No. 60/327,437, filed on Oct. 5, 2001.

(51) Int. Cl.[7] .............................................. A61B 17/00
(52) U.S. Cl. ...................................... 600/213; 600/201
(58) Field of Search ................................. 600/201, 210, 600/213, 214, 215, 216, 217, 219; 606/54, 59, 61, 62, 64, 90, 57, 105; 403/9, 49, 78, 110, 252, 323, 325, 327, 328, 330, 321, 326; 24/376, 461, 523, 524, 599.1, 600.7; 294/82.2, 82.19

(56) References Cited

U.S. PATENT DOCUMENTS

| | | | | |
|---|---|---|---|---|
| 505,281 A | * | 8/1893 | Smith ........................... 280/65 |
| 648,429 A | * | 5/1900 | Peterson ..................... 24/599.1 |
| 838,767 A | * | 12/1906 | Bradley ......................... 278/75 |
| 2,845,307 A | * | 7/1958 | Holmes ........................ 403/49 |
| 4,544,324 A | * | 10/1985 | Hornung ..................... 414/785 |
| 4,631,990 A | * | 12/1986 | Hughes ......................... 81/62 |
| 5,534,002 A | * | 7/1996 | Brumfield et al. ............ 606/61 |
| 5,603,714 A | * | 2/1997 | Kaneda et al. ................ 606/61 |
| 5,683,393 A | * | 11/1997 | Ralph ........................... 606/61 |
| 5,947,966 A | * | 9/1999 | Drewry et al. ................ 606/61 |
| 5,980,523 A | * | 11/1999 | Jackson ........................ 606/61 |
| 5,984,865 A | * | 11/1999 | Farley et al. ............... 600/213 |
| 6,042,540 A | * | 3/2000 | Johnston et al. ............ 600/213 |
| 6,283,967 B1 | * | 9/2001 | Troxell et al. ................ 606/61 |
| 6,324,732 B1 | * | 12/2001 | Arisaka et al. .............. 24/458 |
| 6,438,809 B1 | * | 8/2002 | Camaiani ................... 24/599.4 |
| 6,524,310 B1 | * | 2/2003 | Lombardo et al. ............ 606/61 |
| 6,547,789 B1 | * | 4/2003 | Ventre et al. ................. 606/61 |
| 6,554,832 B2 | * | 4/2003 | Shluzas ........................ 606/61 |
| 6,602,253 B2 | * | 8/2003 | Richelsoph et al. .......... 606/61 |

* cited by examiner

Primary Examiner—Todd E Manahan
Assistant Examiner—David Comstock
(74) Attorney, Agent, or Firm—Stephen J. Stark; Miller & Martin PLLC

(57) ABSTRACT

A surgical retractor has a body and a socket laterally receiving a connector head. The socket cavity is offset from a loading axis extending to the mouth of the slot. The slot laterally receives the connector head as directed towards the socket cavity where it is retained in a locked configuration. The socket cavity is offset from the loading axis.

19 Claims, 1 Drawing Sheet

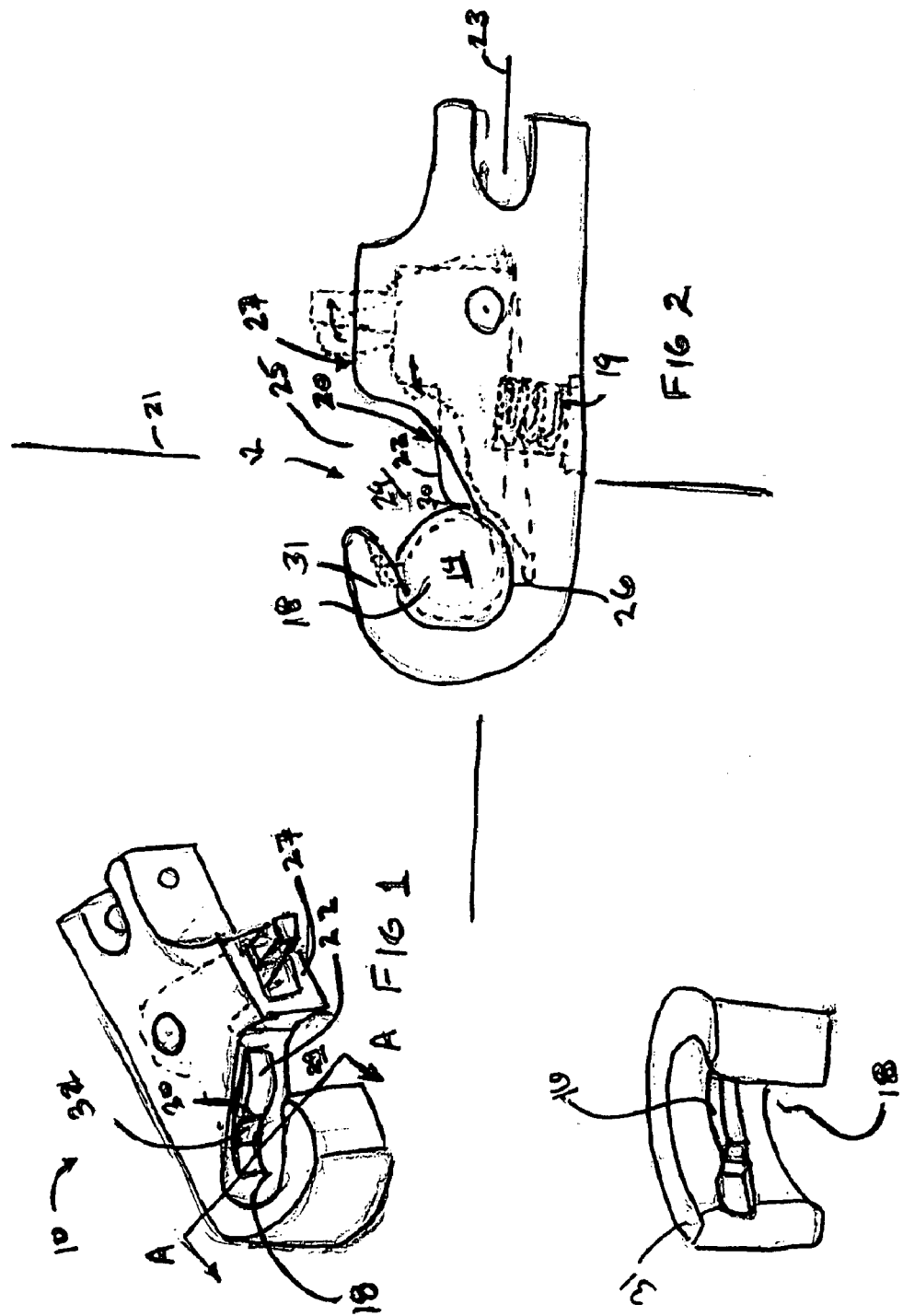

SIDE LOADING SURGICAL RETRACTOR HAVING OFFSET CAVITY

CLAIM OF PRIORITY

This application is a continuation in part of U.S. patent application Ser. No. 10/117,929 filed Apr. 5, 2002, now U.S. Pat. No. 6,733,444 and claims the benefit of U.S. Provisional Patent Application No. 60/327,437 filed Oct. 5, 2001.

FIELD OF THE INVENTION

1. Field of the Invention

The present invention relates generally to a surgical retractor apparatus used with interchangeable retractor blades. More particularly the present invention relates to a surgical retractor adapted to lateral load interchangeable retractor blades.

2. Background of the Invention

When conducting some surgical procedures, it is often desirable to retract tissue. Although there are a number of procedures and devices available to retract tissue, U.S. Pat. No. 6,042,540 allows for the top loading as well as the side loading of retractor blades into a socket. The side loading feature of this, and other prior art, is believed to be advantageous whereby the surgeon's vision is not obscured while connecting, or disconnecting a blade from a retractor. The top loading capability is not believed to be necessary by the Applicant.

The '540 Patent discloses a number of retractors which can utilize the blade of FIG. 1A, specifically, the longitudinal retractor of FIG. 3, the transverse retractor of FIG. 4, and the side-loading hand-held retractor of FIG. 5. As shown in FIGS. 1A and 1C, the blades typically have connector heads locking pins typically extend from opposite sides of the longitudinal axis of the connector head. Although the '540 Patent specifically shows a top loading connector head, other connector heads also employ the opposing locking pin construction.

In the '540 Patent, rotation of cam 130 about pivot 128 locks and unlocks a connector head from within the socket chamber. One of the perceived drawbacks of this cam design is the release lever 124 begins substantially perpendicularly to retractor arms 142 and rotates and extends away from the socket 12 over an arc of about forty degrees as the cam is moved in and out of the socket chamber. Another difficulty is that the '540 Patent allows only for perpendicular side loading. This design may not optimize the width and length of the socket and may be difficult to lock the connector in the socket in some embodiments or to easily tell if the connector is securely loaded in the socket.

Accordingly, a need exists for an improved retractor design.

SUMMARY OF THE INVENTION

A need exists for a surgical retractor which accepts blades having a connector head at least in a lateral loading manner.

Another need exists for a surgical retractor which securely retains connector heads in a socket.

Yet another need exists for a side loading surgical retractor socket which allows a connector head to "snap" in to a locked configuration without a need for an operator to manually operate or reset a locking mechanism.

Another need exists for a non-moving portion of the socket to assist in retracting the connector head in a locked position to take at lease some of the lock during retraction.

Accordingly, a surgical retractor includes a body having a socket for receiving a connector head. The socket has a release which moves a lock toward and away from a connector head when positioned within the socket. The lock may rotate as illustrated or slide as shown in co-pending application Ser. No. 10/117,929, incorporated by reference. A convex surface on a first face of the lock allows for the connector head to be pushed into position or "snapped" in, while a convex surface on a second face of the lock is believed to assist in retaining an inserted connector head in position within the socket. The socket is preferably constructed to have an interior ledge which would prevent top loading of sockets and angularly offset in a lateral direction. The angular offset of the socket is a J-channel. As the connector head is loaded, it moves off the perpendicular loading axis to a locked position.

BRIEF DESCRIPTION OF THE DRAWINGS

The particular features and advantages of the invention as well as other objects will become apparent from the following description taken in connection with the accompanying drawings in which:

FIG. 1 is a top elevational view of a side-loading retractor arm portion of the preferred embodiment of the present invention;

FIG. 2 shows a top view of the surgical retractor of FIG. 1 with internal portions shown in phantom; and FIG. 3 is a perspective cross sectional view taken along the line A—A of FIG. 1.

DETAILED DESCRIPTION OF THE PREFERRED EMBODIMENT

FIG. 1 illustrates a preferred embodiment of a surgical retractor arm portion 10 having at least one socket 12. This arm can be utilized instead of the arm shown in U.S. Pat. No. 6,042,540. Other retractor designs may also utilize the socket 12 of the present invention. The socket 12 of this design receives a connector head 14 in a lateral loading manner as shown in FIG. 2. In fact, at least one protuberance, such as one or more pins, or ledge 16 shown in FIG. 3, prevent a connector head 14 from being top loaded in the preferred embodiment as the pins 16 extend into the socket chamber 18 and are preferably received within a lateral groove in the connector head 14.

In alternative embodiments, top loading may be allowed, such as if the ledge 16 is not provided, does not sufficiently extend within the socket chamber 18, or otherwise. The connector head 14 shown and described in co-pending and co-owned patent application Ser. No. 60/327,437 incorporated by reference works well with the socket 12 of the preferred embodiment. This particular connector head design has a cap that prevents top loading. Other connector heads could also be utilized.

Instead of using a cam which rotates as shown and described in the '540 Patent to secure a connector head within the socket chamber as shown in FIG. 2, the preferred embodiment may utilizes a linearly moving lock, as shown and described in co-pending application Ser. No. 10/117,929 or a pivoting lock 20 as shown in the Figures. The lock 20 is moveable between a locked position as shown in FIG. 2, and an unlocked position shown in phantom in FIG. 2.

The lock 20 has a first face 22 which is directed outward from the socket cavity 18. The first face 22 is preferably convex so that when a connector head 14, which is traditionally cylindrical in shape, is pushed against the first face 22, the lock 20 is deflected into slot 26. The slot 26 receives the lock 20 as it is deflected.

A spring 19 normally biases the lock 20 into the locked position shown in FIG. 2. Accordingly, when the bias of spring is overcome by a connector head 14 being directed within the socket cavity 18, the connector head 14 "snaps" into position since once the head clears the tip 30 of the lock 20, it encounters second face 32 which is concave. The concave shape of the second face 32 is believed to be advantageous as it may allow for the circular shape of the socket cavity 18 to be continued so that a circle inscribed along the socket walls 34 would continue along the second face 32. Furthermore the concave shape of the second face 32, in the preferred embodiment, prevents the second face 32 from being positioned in the socket cavity 18.

The socket cavity 18 is offset in the preferred embodiment as illustrated. In the prior art, lateral insertion of a connection head into a socket was done only along loading axis also referred to as perpendicular axis 21 which was perpendicular to support axis 23 extending along the retractor arm 10. In the preferred embodiment the connector head 14 may begin the insertion process along perpendicular axis 21, but must travel angularly off this perpendicular axis 21 to the locked position in the socket cavity 18 shown in FIG. 2.

Adjacent to, and in communication with, the socket cavity 18 is a recess 36 which may accept a fixing pin of a connector head. Furthermore, other recesses or notches may also accept a second fixing pin of a connector head at least partially therein to assist in prevent the locking pin from rotating.

While the connector head 14 may be snapped into the socket cavity 18 as explained above, the lock 20 may be operated with the trigger 40. The trigger 40 may also be curved to accommodate a user's thumb or finger. The trigger is connected to the lock 20 by arm 44. Movement of the trigger 40 pivots the lock 20 into and out of the locking position accordingly.

While many aspects differentiate the preferred embodiment from the design shown and described in the '540 Patent, many of the new aspects of this disclosure could be advantageously incorporated into that design as well.

When loading the connector head 14 into the cavity 18, the connector head is laterally loaded along perpendicular axis 21 into mouth 25 located on the side 27 of the retractor 10. Although the connector head in the preferred embodiment is initially loaded perpendicularly into the mouth 12, in some embodiments it may be possible that the mouth 25 allows for the direct offset insertion of the connector head 14, i.e., angularly relative to perpendicular axis 21. After entering the mouth and traveling into slot 29, the connector head 14 reaches its furthermost insertion of direct perpendicular insertion. At this point in time, the connector head 14 is displaced at least some degree perpendicularly to the perpendicular axis 21. In the preferred embodiment it is also displaced an additional amount along the travel of the perpendicular axis 21 as shown in FIG. 2. Eventually the connector head 14 reaches the socket cavity 18 which is preferably located at the end of slot 29.

Once in the socket cavity 18 with the lock 20 in place as described above, the connector head 14 is retained as shown in FIG. 2 by the lock 20 as well as the socket cavity 18. In particular, the leg 31 at least partially assists the lock 20 in retaining the connector head 14 from direct movement solely along the perpendicular axis 21 out of the socket cavity 18. In the prior art, the moveable locking mechanism was the only means of restraining the connector head 14 within the socket cavity when pulled along the perpendicular axis 21. Accordingly, if the lock 20 were to fail, the connector head 14 would immediately be released from the socket cavity 18. In the presently preferred embodiment of the present invention, the leg 31 assists in retaining the connector head 14 in the locked position and bears a significant portion, if not all of the perpendicular of the forces along outward movement along the perpendicular axis 21.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

What is claimed is:

1. A surgical retractor comprising:
   a connector head;
   a retractor body having a top, bottom, and sides, and a laterally loading mouth in one of the sides of the retractor body leading to a socket cavity for receiving the connector head, said mouth having a loading axis extending perpendicularly to the one of the sides having the mouth, said loading axis angularly offset by an angular offset from the loading axis said angular offset non-parallel to the loading axis; with a leg formed as a part of the retractor body adjacent the mouth and the socket cavity; and
   a displaceable lock configured to selectively retain and release connector head within the socket cavity in a locked position; and wherein at least a portion of the leg at least assists in preventing outward lateral movement of the connector head from the socket cavity parallel to the loading axis; and
   said lock normally biased in the locked position.

2. The surgical retractor of claim 1 wherein the lock has a first face outwardly oriented relative to the socket cavity having a convex surface.

3. The surgical retractor of claim 1 further comprising a trigger connected to the lock.

4. The surgical retractor of claim 3 wherein movement of the trigger moves the lock into a disengaged position.

5. The surgical retractor of claim 1 wherein the angular offset is at about forty-five degrees relative to the loading axis.

6. The surgical retractor of claim 1 wherein the lock further comprises a first face inwardly oriented relative to the socket cavity having a concave surface.

7. The surgical retractor of claim 1 wherein the lock further comprises a first face and the socket cavity is at least partially surrounded by socket walls and the first face has a similar arc of curvature as the socket walls.

8. The surgical retractor of claim 1 wherein when a connector head is in the locked position at least one of the lock and socket retains the connector head from lateral removal.

9. The surgical retractor of claim 1 further comprising at least one stationary protuberance in the socket cavity preventing top loading of the connector head.

10. The surgical retractor of claim 1 wherein the lock moves along an operation axis perpendicular to a longitudinal axis through the connector head.

11. The surgical retractor of claim 1 wherein as the connector head is inserted into the socket, the connector head moves a distance along a support axis of the surgical retractor.

12. The surgical retractor of claim 1 wherein the slot is symmetrical about a loading axis, said loading axis substantially perpendicular to the support axis.

13. The surgical retractor of claim 12 wherein the slot is angled relative to the socket cavity.

14. A surgical retractor comprising:

a connector head;

a socket body having a lateral loading mouth for receiving the connector head along a side of the socket body along a loading axis;

a slot within the socket body; said slot connecting the mouth to a socket cavity, said slot angularly offset along an offset axis from the loading axis, said slot adjacent to a leg formed in the socket body adjacent to the socket cavity and mouth; and a displacable lock configured to selectively move at least partially within the slot in a locked position and having a released position allowing the connector head to move out of the socket cavity; and when in the locked position, said lock spaced from the mouth; and the leg assisting in retaining said connector head in the locked position from lateral movement out of the socket cavity towards the mouth in a parallel direction to the loading axis.

15. The surgical retractor of claim 14 wherein the lock has a convex first face outwardly directed from the socket cavity and a concave second face inwardly directed to the socket cavity.

16. the surgical retractor of claim 14 wherein the slot is angled relative to the socket cavity.

17. A surgical retractor comprising:

a connector head;

a socket body having a leg and a lateral loading mouth for receiving a the connector head;

a slot and a socket cavity within the socket body, said slot connected to the mouth, said slot communicating the socket cavity with the mouth and spacing the socket cavity from the mouth, said mouth having a loading axis extending therethrough in the lateral direction, and said socket cavity angularly offset at an angle from the loading axis at an angular offset, said socket cavity symmetrically oriented relative to the angular offset, and said angular offset non-parallel to the loading axis, and said leg obstructing outward lateral movement in a direction parallel to the loading axis;

and a displaceable lock moveable at least partially within the slot into a locked position, and a release position to release the connector head from the socket cavity.

18. The surgical retractor of claim 17 wherein the slot is centered about the loading axis.

19. The surgical retractor of claim 17 wherein the slot is angled relative to the socket cavity.

* * * * *